(12) United States Patent
Wany

(10) Patent No.: US 9,993,140 B2
(45) Date of Patent: Jun. 12, 2018

(54) ENDOSCOPIC ARRANGEMENT

(71) Applicant: AWAIBA CONSULTADORIA, DESENVOLVIMENTO E COMÉRCIO DE COMPONENTES MICROELECTRÓNICOS, UNIPESSOAL, LDA, Madeira (PT)

(72) Inventor: Martin Wany, Yverdon-les-Bains (CH)

(73) Assignee: AWAIBA CONSULTADORIA, DESENVOLVIMENTO E COMÉRCIO DE COMPONENTES MICROELECTRÓNICOS, UNIPESSOAL, LDA, Madeira (PT)

( * ) Notice: Subject to any disclaimer, the term of this patent is extended or adjusted under 35 U.S.C. 154(b) by 246 days.

(21) Appl. No.: 14/311,823

(22) Filed: Jun. 23, 2014

(65) Prior Publication Data

US 2014/0300698 A1    Oct. 9, 2014

Related U.S. Application Data

(63) Continuation of application No. PCT/CH2012/000280, filed on Dec. 21, 2012.

(30) Foreign Application Priority Data

Dec. 23, 2011    (CH) ..................................... 2047/11

(51) Int. Cl.
*A61B 1/00*    (2006.01)
*A61B 1/05*    (2006.01)
(Continued)

(52) U.S. Cl.
CPC ...... *A61B 1/00193* (2013.01); *A61B 1/00114* (2013.01); *A61B 1/05* (2013.01);
(Continued)

(58) Field of Classification Search
CPC .... A61B 1/00114; A61B 1/05; A61B 1/00006
(Continued)

(56) References Cited

U.S. PATENT DOCUMENTS 4,667,229 A * 5/1987 Cooper ................. H04N 9/045
348/249
4,746,975 A * 5/1988 Ogiu ........................ A61B 1/05
348/76
(Continued)

FOREIGN PATENT DOCUMENTS

EP    2108943 A2    10/2009
JP    H07312710 A    11/1995
(Continued)

OTHER PUBLICATIONS

Article by M. Wany et al. SPIE in the magazine "Photonics West" of Jan. 2009. Reference: EI09-EI114-9_7249-32, See Specification, p. 2 [To follow].

(Continued)

*Primary Examiner* — Jeffery Williams
(74) *Attorney, Agent, or Firm* — McDermott Will & Emery LLP

(57) ABSTRACT

The endoscopic arrangement (10) is provided with a plurality of image sensors (11), a distal end (10a) and a proximal end (10b). Each of the image sensors is arranged to generate a proper sensor clock, which can be influenced by control electronics at the proximal end of the endoscope arrangement so that such sensor, or a plurality of such sensors, can be operated synchronously with each other or synchronously with a clock set externally. The control electronics is provided with mechanism for detecting the sensor clock and/or the sensor frame rate and/or the sensor image phase and adjusting the detected information to a reference clock.

14 Claims, 4 Drawing Sheets

(51) Int. Cl.
*H04N 5/374* (2011.01)
*H04N 5/225* (2006.01)
*H04N 5/232* (2006.01)
*H04N 5/376* (2011.01)
*G02B 23/24* (2006.01)

(52) U.S. Cl.
CPC ......... *G02B 23/2484* (2013.01); *H04N 5/374* (2013.01); *A61B 1/00006* (2013.01); *G02B 23/2415* (2013.01); *H04N 5/23203* (2013.01); *H04N 5/3765* (2013.01); *H04N 2005/2255* (2013.01)

(58) Field of Classification Search
USPC .......................................................... 348/45
See application file for complete search history.

(56) References Cited

U.S. PATENT DOCUMENTS

| | | | | |
|---|---|---|---|---|
| 5,614,943 | A | * | 3/1997 | Nakamura ......... A61B 1/00105 348/72 |
| 2004/0073086 | A1 | | 4/2004 | Abe |
| 2006/0126176 | A1 | * | 6/2006 | Nogami ............... A61B 1/0005 359/464 |
| 2007/0149847 | A1 | * | 6/2007 | Shimada ............ A61B 1/00055 600/118 |
| 2009/0216080 | A1 | * | 8/2009 | Nakamura ......... H04N 5/23203 600/109 |
| 2009/0266999 | A1 | | 10/2009 | Krattiger |
| 2010/0225729 | A1 | * | 9/2010 | Fujise ..................... B41J 2/473 347/224 |
| 2010/0240991 | A1 | * | 9/2010 | Bartlett ................ A61B 5/0002 600/437 |

FOREIGN PATENT DOCUMENTS

| | | |
|---|---|---|
| JP | 2004049770 A | 2/2004 |
| JP | 2005244454 A | 9/2005 |
| WO | 2007101360 A1 | 9/2007 |

OTHER PUBLICATIONS

Article M. Wany et al. "Ulta small digital image sensor for endoscopic applications" Proc. of 2009 International Image Workshop, Mar. 26, 2009 XP55035306, Bergen, Norway, See Specification, p. 2 [To follow].

Japanese Examination Report issued in corresponding Japanese Patent Application No. 2014-547656 dated Nov. 8, 2016.

* cited by examiner

ENDOSCOPIC ARRANGEMENT

This application is a continuation of PCT/CH2012/000280 filed Dec. 21, 2012 which claims priority from Swiss Application No. 2047111 filed Dec. 23, 2011.

FIELD OF THE INVENTION

The invention relates to an endoscopic arrangement with a plurality of image sensors at the distal end, each of the image sensors being arranged to generate a proper sensor clock, which can be influenced by control electronics at the proximal end of the endoscope arrangement.

When the term "image phase" is used in this disclosure, this means the phase of the image capture sequence of several image sensors with respect to each other of the phase of the image capture of one image sensor with respect to an external clock (e.g. to a pulsed light source). This is not to be confused with the capture of a "phase image". In this last case, information is determined from every pixel about the phase position of a frequency entering on this pixel and transmitted as a visual signal, while the image phase, within the framework of this invention, is not used to transmit information about the viewed object, but is important in order to be able to operate e.g. a plurality of image sensors in such a synchronous way that all these image sensors can be lighted with one single pulsed light source.

BACKGROUND OF THE INVENTION

Endoscopes are often used for medical examinations, interventions and analyses. Endoscopes with the smallest diameter possible are used in order to reach the examination or operation site passing through naturally existing body orifices or by means of little traumatic steps. Traditionally, such endoscopes are produced by bundles of optical fibers. Today, the CMOS sensor technology is increasingly used, wherein a miniaturized image sensor is placed directly on the distal end of the endoscope to transmit the image in the form of an electrical signal.

Image sensors for use on the distal end of medical endoscopes are mostly structured today in such a way that they can operate to a large extent autonomously and are connected to the proximal end only via a data line and the power supply. The addition of a clock line is generally not desirable because of the additional sensor contacts and additional signal lines required for the clock. This is why an oscillator, which defines the sensor clock autonomously, is integrated in such sensors. The simplest form uses a digital ring oscillator. Refer in particular to the article by M. Wäny et. al. SPIE in the magazine "Photonics West" of January 2009. Reference: E109-E1114-9_7249-32. This kind of embodiment has the disadvantage that the sensor clock is only determined approximately and is strongly influenced by fluctuations in the manufacturing process and by operating conditions such as e.g. the operating temperature.

The realization of frequency-stable oscillators, with a stability as it is known e.g. from quartz oscillators, is not possible purely in CMOS technology. The clock signal generated by such a purely CMOS oscillator shows large fluctuations compared with a clock signal generated by a quartz oscillator, especially when the sensor temperature varies or the power supply is subjected to fluctuations. In article M. Wäny et al. "Ultra small digital image sensor for endoscopic applications" Proc. of 2009 International Image Sensor Workshop, 26 Mar. 2009 (2009-03-26) XP55035306, Bergen, Norway, techniques are described in order to make a miniaturized image sensor more robust with respect to the influence on its functions, among others also with respect to the influence of the environmental conditions on its operating frequency. But possibilities or methods to adjust such an autonomously operating sensor to a clock set externally are missing. Capturing the images however often requires to operate the sensor synchronously with an external clock, to allow sending the image data without intermediate storage to a video output device such as e.g. a video monitor. There are also applications, e.g. the stereoscopic image capture, for which it is advantageous to operate a plurality of image sensors synchronously with respect to each other.

The international publication WO 2007/101360 A1 relates to a miniaturized image sensor for a smallest-size endoscope, which operates autonomously and generates its sensor clock itself. But the publication lacks methods or possibilities to operate several such image sensors synchronously with each other or such image sensor synchronously with a clock set externally (e.g. coming from a pulsed lighting).

The European patent application EP 2 108 943 A2 describes a device for fluorescence imaging including light generation means. However, the lighting sources described in this publication have to be synchronized by means of a control device with respect to the image frequency of the image sensor, there is no possibility to synchronize the image sensor with respect to the lighting frequency. This publication also mentions the use of a plurality of image sensors for capturing 3D image data, but there is no possibility to synchronize the image sensors with respect to each other. This will lead easily to artifacts and miscalculations, in particular when capturing 3D images with objects that move in the image, since the distance traveled by an object moving in the image during the time lag between the respective image captures by the two sensors will be considered wrongly as a depth information.

SUMMARY OF THE INVENTION

Since the restricted space available on the tip of the endoscope makes it desirable to be able to place the electronics on the image sensor, the invention aims to reduce the electronics on the image sensor sufficiently to use, insofar possible, the whole surface of the sensor for the actual image capture, while the image sensor is to operate on the one hand autonomously, in particular without the supply of an external clock signal but, on the other hand, it is to capture and transmit simultaneously the single images synchronously with an external clock or synchronously with a plurality of image sensors.

The surprising solution to this consists in providing the control electronics with means for detecting the sensor clock and/or the sensor frame rate and/or the sensor image phase and adjusting it to a reference clock.

Therefore, the invention proposes an endoscopic arrangement characterized in that the control electronics is provided with means for detecting the sensor clock and/or the transmitted sensor frame rate and/or the sensor image phase of each individual sensor of said plurality of sensors and for comparing its value with the corresponding values of the other sensors and adjusting all or a part of the sensors of said plurality of sensors to each other, and in that the regulation of the image frequency occurs by adjusting the supply voltage.

The sensor allows, with a simple purely CMOS oscillator on the image sensor, to capture and transfer the images synchronously to an external clock and/or to synchronize a plurality of sensors with each other and transfer the image data synchronously.

The sensor embodiment according to the invention allows extending the functionality of the image sensor without requiring sensor surface for additional electronics.

The endoscopic arrangement has preferably one or a plurality of image sensors at the distal end, each of which generating its proper sensor clock, which can be influenced by control electronics at the proximal end of the endoscope arrangement, said control electronics including means for detecting the sensor clock and/or the transmitted sensor frame rate and/or the sensor image phase of each individual sensor of said plurality of sensors and for comparing its value with the corresponding values of the other sensors and adjusting all or a part of the sensors of said plurality of sensors to each other.

Said image sensors are advantageously manufactured in CMOS (Complementary Metal Oxide Semiconductor) technology.

The endoscopic arrangement according to the invention is advantageously designed so that influencing the sensor clock can occur by modifying the sensor supply voltage.

The endoscopic arrangement according to the invention is advantageously designed so that influencing the sensor clock can occur by transmitting configuration data via an image data interface from said control electronics to the sensor and that the sensor can process said configuration data and modify the sensor clock generation frequency according to the configuration data.

The endoscopic arrangement according to the invention is advantageously designed so that said configuration data can be transmitted multiplexed via the image data interface.

The endoscopic arrangement according to the invention is advantageously designed so that said configuration data can be transmitted every time after the transmission of an image line.

The endoscopic arrangement according to the invention is advantageously designed so that said configuration data can be transmitted every time after the transmission of an image.

The endoscopic arrangement according to the invention is advantageously designed so that the stereoscopic analysis of the image data of the plurality of image sensors allows generating 3D image data.

The endoscopic arrangement according to the invention is advantageously designed so that said image sensors can be synchronized with a pulsed light source.

BRIEF DESCRIPTION OF THE DRAWINGS

An embodiment example of the invention is described below in reference to the drawings. The drawings represent.

DETAILED DESCRIPTION OF THE DRAWINGS

Figure 1:
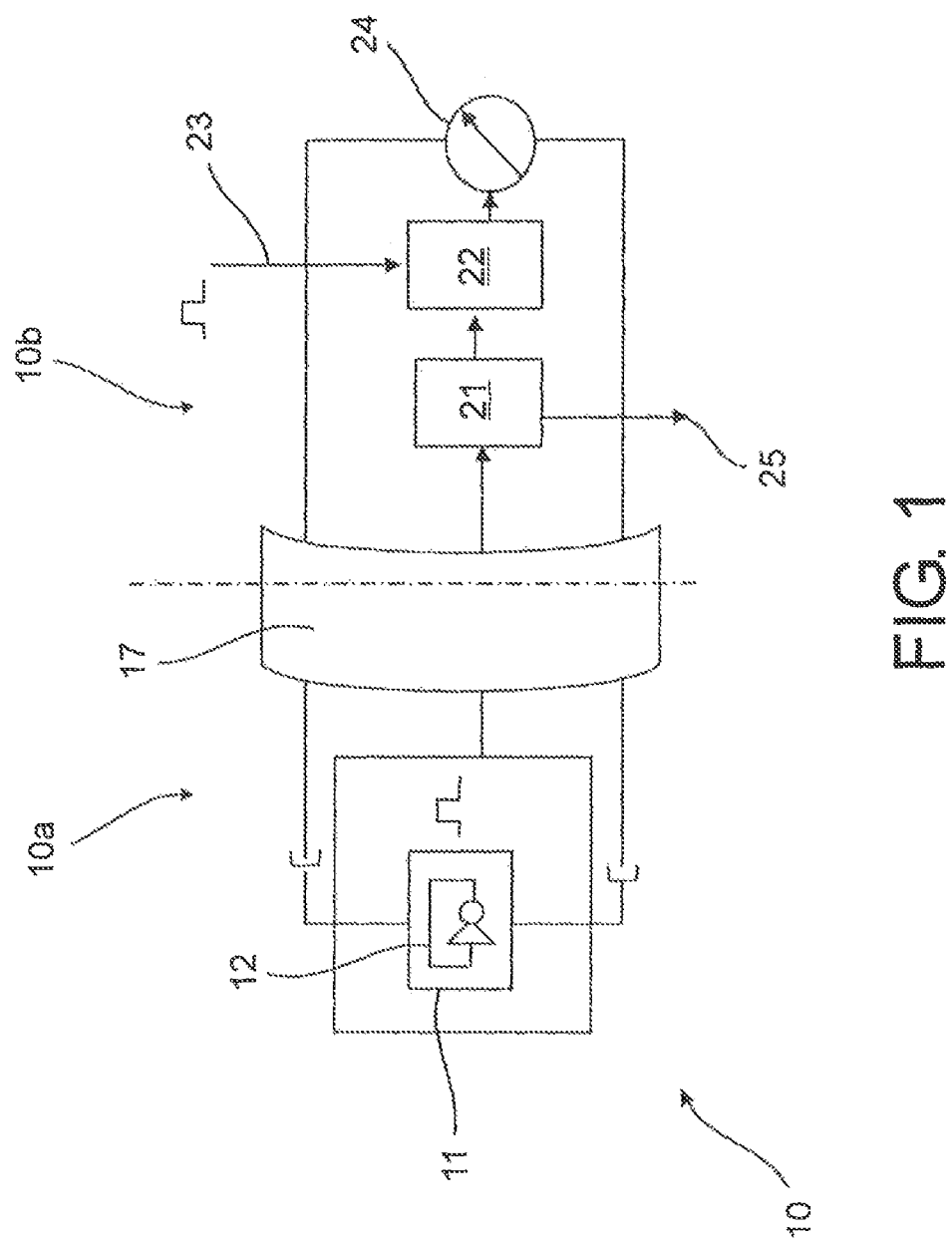
FIG. 1 represents a block diagram of an endoscope with adjustment of the image sensor clock generation by means of sensor supply voltage regulation.

The possibilities of realizing the endoscopic arrangement according to the invention disclosed in the drawings must be understood merely as illustrative examples. The examples do not restrict the general nature of the invention.

FIG. 1 shows the simplest realization of an endoscope arrangement 10 according to the invention with a distal side 10a and a proximal side 10b provided with an image sensor 11, in which the clock is realized by means of a simple ring oscillator 12.

Figure 2:
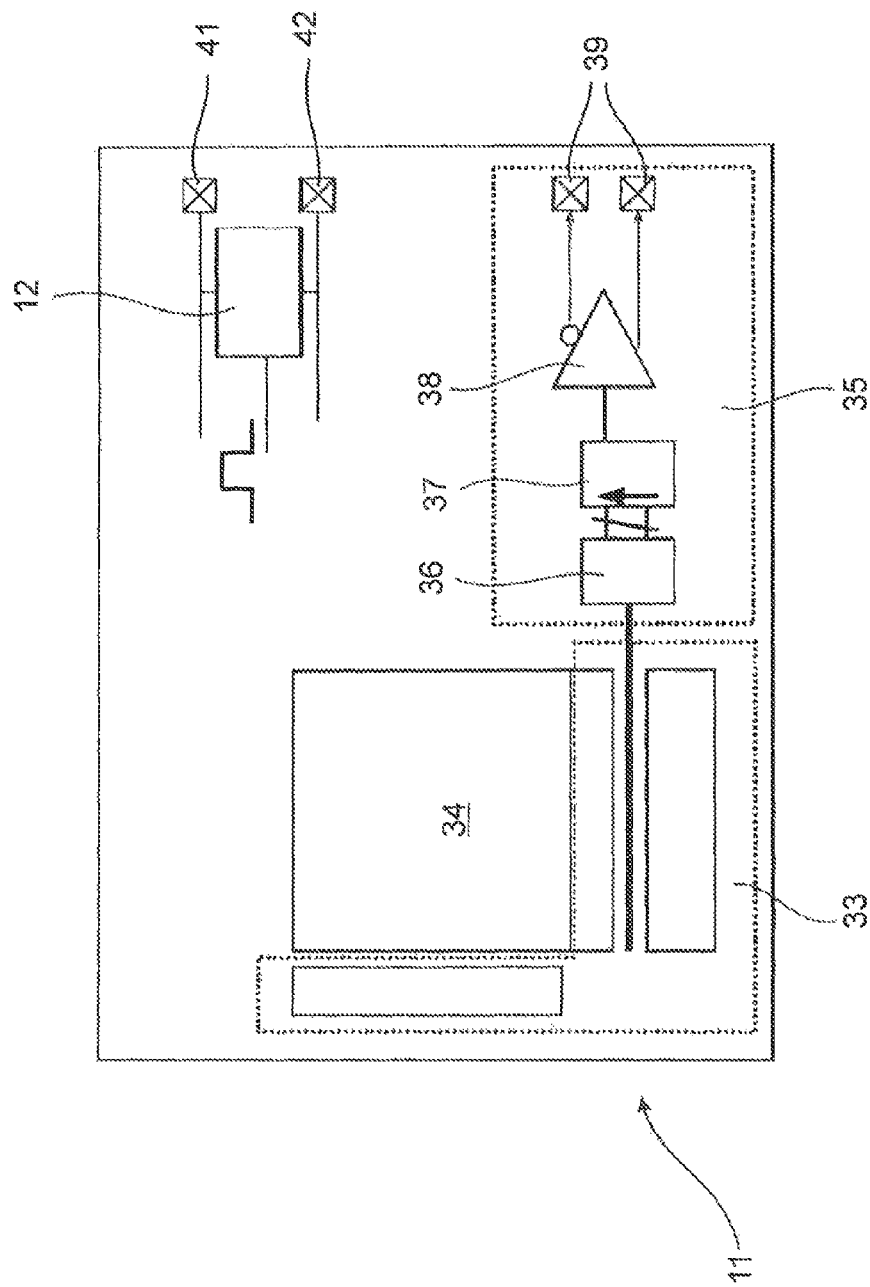
FIG. 2 represents a block diagram of an image sensor suitable for integration in an endoscope tip.
Figure 3:
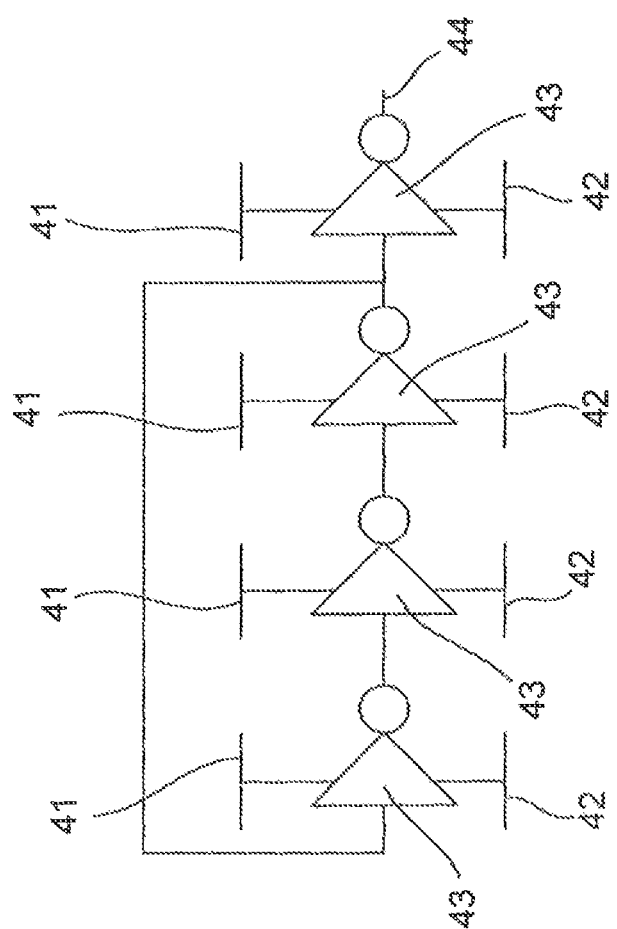
FIG. 3 shows a ring oscillator with a chip power supply for generating a basic chip clock.

The image sensor is described further in FIG. 2 and the ring oscillator in FIG. 3. The image sensor 11 is connected to the control and processing electronics in the proximal section by means of a data and power supply cable 17. The image sensor 11 used in the endoscope arrangement 10 has advantageously possibilities of transmitting the pixel clock generated on the image sensor or a constant divider of it in the data stream, for example using line and image start/end synchronization pulses. Moreover, the endoscope arrangement 10 is provided in the proximal section or in a control and display device connected to the endoscope arrangement 10 with means 21 allowing to detect the pixel clock or the line clock, but at least the frame clock, transmitted by the image sensor, and means 22 allowing to compare it with a reference clock 23. The endoscope arrangement 10 is also provided in the proximal section 10b with an image data display interface (e.g. a video monitor connection) 25. Furthermore, the endoscope arrangement 10 is provided in the proximal section 10b or in a control and display device connected to the endoscope arrangement 10 with means for adjusting the sensor supply voltage 24 so that, when detecting a difference between the clock sent by the sensor and the corresponding reference clock, the sensor clock can be accelerated or slowed down according to whether this difference is positive or negative. According to the current knowledge of the control and regulation technology, the image sensor supply voltage correction is designed so that a stable sensor clock is achieved after a certain adjustment time.

FIG. 2 shows a simplified block diagram of the image sensor 11 used in the endoscope arrangement 10. Said image sensor 11 includes a control 33 for reading a pixel matrix 34 and, according to the known technique, suitable electronics for transmitting the image data through a data transmission channel 35 consisting for example of an analog-digital converter 36, a data serialization 37 and a differential signal driver 38, as well as a differential data interface 39. The sensor clock is generated by a ring oscillator 12 powered proportionally by the chip supply voltage 41 and 42.

FIG. 3 shows in detail a ring oscillator 12 realized for example as a circuit and generating the chip clock. The ring oscillator generates a periodic chip clock by connecting an odd number of signal-inverting circuit elements in a ring. In the embodiment example of FIG. 3, three digital inverters 43 are connected in a ring. Each of the inverter blocks is powered between the chip supply voltage 41 and the chip ground potential 42. Immediately after applying the chip supply voltage, the circuit starts oscillating at its characteristic proper frequency. A simple amplifier circuit in the form of an additional inverter 43 taps the signal of the oscillator ring and provides it with a low impedance as an output signal 44. The proper frequency of the ring oscillator is higher when it is supplied with a higher voltage; accordingly, a lower supply voltage results in a lower oscillation frequency. Alternatively, the ring oscillator can also be supplied with another voltage proportional to the supply voltage.

In an alternative implementation of the endoscope arrangement, the image sensor has possibilities of receiving configuration data from the proximal control and processing electronics and to adjust gradually the sensor clock frequency using this configuration data. Therefore, the sensor is provided with means for accelerating or slowing down the sensor clock. The step size of said image sensor clock regulation is designed in compliance with known control technology rules so that a stable regulation of the image phase and of the sensor clock frequency is possible. It is in particular possible to adjust the sensor clock frequency in small continuous steps until reaching a target frequency and a target phase position for the image capture. The configuration data can be transmitted, according to the known state of electronic data communication, as well through a separate configuration line as multiplexed through the image data lines. The configuration data transmission for sensor clock frequency adjustment can take place as well continuously as at specific moments, e.g. every time after the complete transmission of an image line or after the transmission of a complete image. The larger the transmission intervals of said configuration data, the finer the frequency adjustment steps must be, and the more time will be required to synchronize the image sensor with a reference clock or a plurality of sensors with each other.

Figure 4:
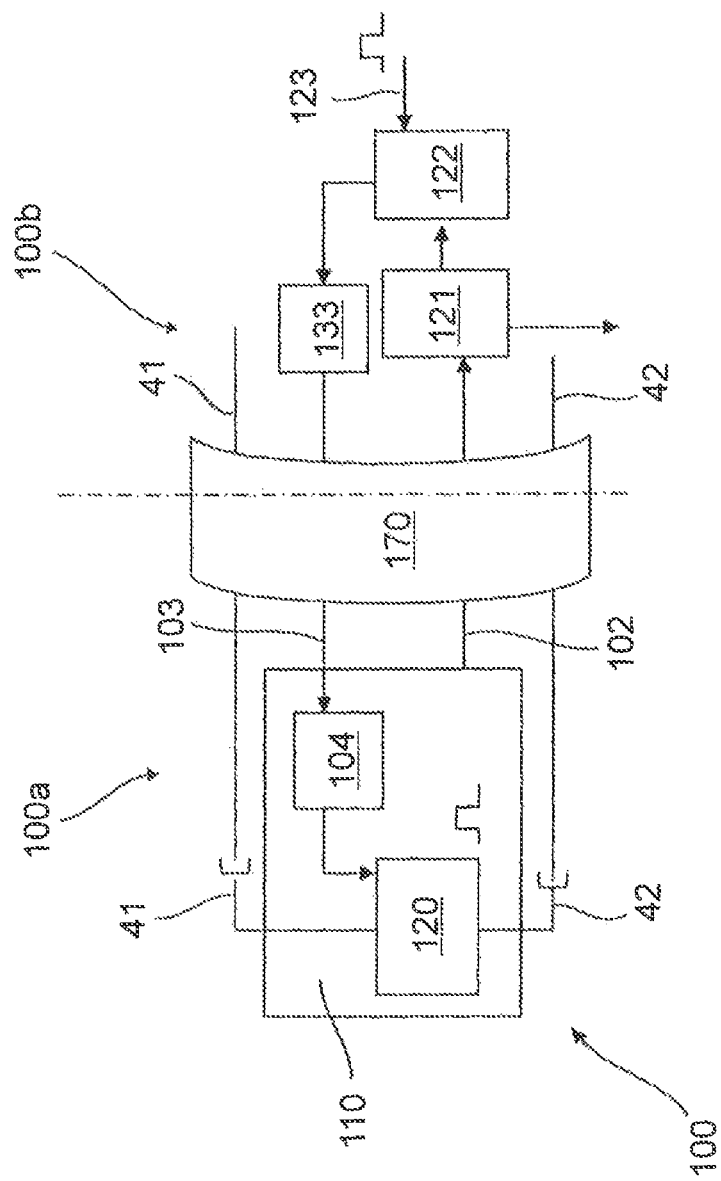
FIG. 4 represents a block diagram of an endoscope with adjustment of the image sensor clock generation by means of a configuration interface.

FIG. 4 shows a block diagram of the endoscope arrangement 100 according to this variant and shows schematically the functional groups necessary for the regulation of the sensor clock.

The endoscope arrangement 100 consists of a distal section 100a and a proximal section 100b. The distal and proximal sections are connected together via a data and power supply cable 170. The image sensor 110 used in the alternative endoscope arrangement is provided with means 104 for receiving communication data via a communication data interface 103 and processing this data. The image sensor 110 is powered with the supply voltage 41 and the ground potential 42 which, in this variant of the endoscope arrangement according to the invention, are fixed. The image sensor is also provided with means for adjusting the frequency of an oscillator 120 according to the control commands of the processed communication signals. According to the known technique, this can for example be achieved by means of a "voltage-controlled oscillator" controlled by means of a digital-analog converter. Moreover, the alternative endoscope arrangement 100 is provided in the proximal processing electronics 100b with means 121 allowing to detect the pixel clock or the line clock, but at least the frame clock, transmitted by the image sensor, and means 122 allowing to compare it with a reference clock 123. The arrangement is also provided with means 133 for sending back communication data to the image sensor. Depending whether the detected sensor clock is higher or lower than the reference clock, the oscillator 120 on the image sensor 110 is reconfigured, according to known control and regulation technique rules, via communication interface 103 and 104 so that, after a certain adjustment time, a stable sensor clock results, whose frequency and phase are equal to those of the reference clock.

The invention claimed is:

1. An endoscopic arrangement (10, 100) with a plurality of image sensors (11, 110) located at and integrated into a distal end (10a, 100a) thereof, each of the image sensors being arranged to generate a sensor clock, which can be influenced by control electronics located at and integrated into a proximal end (10b, 100b) of the endoscope arrangement,
wherein the distal end (10a, 100a) is spaced from the proximal end (10b, 100b),
the control electronics is arranged for detecting at least one of the sensor clock, a transmitted sensor frame rate, and a sensor image phase of one image sensor, of the plurality of image sensors, and for comparing a value of the sensor clock, the transmitted sensor frame rate or the sensor image phase of the one image sensor, of the plurality of image sensors, with a corresponding value of another image sensor, of the plurality of image sensors, and adjusting the value of the one image sensor, of the plurality of image sensors, to the value of the other image sensor, of the plurality of sensors, and regulation of an image frequency and/or an image phase occurs by adjusting a sensor supply voltage,
each of the plurality of image sensors (11, 110) are electrically connected to the control electronics, located at the proximal end, via the data and power supply cable (17), and
the sensor clock, for each one of the image sensors, is a local clock which is carried by the respective image sensor at the distal end of the endoscopic arrangement, and the control electronics, located at the proximal end of the endoscope arrangement, facilitates adjustment of each one of the sensor clocks, of the plurality of image sensors, by a signal received from a reference clock which is located external to the distal end of the endoscopic arrangement.

2. The endoscopic arrangement according to claim 1, wherein the image sensors are manufactured by CMOS (Complementary Metal Oxide Semiconductor) technology and the proximal end of the endoscope arrangement is provided with voltage adjustor which adjusts the sensor supply voltage so that, when the endoscope arrangement detects a time difference between one or more of the sensor clocks, of the plurality of image sensors, and the reference clock, the one or more sensor clock, of the plurality of image sensors, can be either accelerated or slowed down according to whether this difference is positive or negative.

3. The endoscopic arrangement according to claim 1, wherein the endoscopic arrangement is designed so that influencing the sensor clock occurs by modifying the sensor supply voltage and the image sensor receives configuration data from the control electronics and a sensor clock frequency of the sensor clock is adjusted using the configuration data.

4. The endoscopic arrangement according to claim 1, wherein the endoscopic arrangement is designed so that influencing the sensor clock occurs by transmitting configuration data, via an image data interface, from the control electronics to the sensor and the image sensor can process the configuration data and modify a frequency of the sensor clock according to configuration data, and synchronization occurs via a power line or a data line using the sensor supply voltage to adjust an oscillator or using configuration data to adjust a frame rate or an image phase of the image sensor so that the image sensor receives a signal indicative of the reference clock.

5. The endoscopic arrangement according to claim 4, wherein the endoscopic arrangement is designed so that the configuration data can be transmitted multiplexed via the image data interface, and the image sensor includes a control for reading a pixel matrix, and electronics for transmitting image data through a data transmission channel having an analog-digital converter, a data serialization, a differential signal driver and a differential data interface, and the image clock is generated by an oscillator powered proportionally by a chip supply voltage.

6. The endoscopic arrangement according to claim 5, wherein the endoscopic arrangement is designed so that the configuration data can be transmitted every time after the transmission of an image line, and synchronization occurs, via a power line or a data line, using the sensor supply voltage to adjust an oscillator or using configuration data to adjust frame rate or image phase of the image sensor.

7. The endoscopic arrangement according to claim 5, wherein the endoscopic arrangement is designed so that the configuration data can be transmitted every time after a transmission of an image.

8. The endoscopic arrangement according to claim 1, wherein stereoscopic analysis of image data of the plurality of image sensors allows generating 3D image data.

9. The endoscopic arrangement according to claim 1, wherein the endoscopic arrangement is designed so that the image sensors can be synchronized with a pulsed light source.

10. The endoscopic arrangement according to claim 1, wherein a data and power supply cable (17) is located between the image sensors (11, 110) at the distal end (10a, 100a) and the control electronics at the proximal end (10b, 100b).

11. The endoscopic arrangement according to claim 1, wherein each one of the plurality of image sensors (11, 110) communicates with the control electronics via a single communication line, connected with the data and power supply cable (17), so that each one of the plurality of image sensors (11, 110) transmits both information about a viewed object and at least one of the sensor clock, the transmitted sensor frame rate, and the sensor image phase of one image sensor via the single communication line.

12. The endoscopic arrangement according to claim 1, wherein the sensor clock is accelerated when the means for adjusting the sensor supply voltage detects a positive difference between the clock sent by the sensor and the reference clock, while the sensor clock is slowed down when the means for adjusting the sensor supply voltage detects a negative difference between the clock sent by the sensor and the reference clock.

13. An endoscopic arrangement (10, 100) with a plurality of image sensors (11, 110) located at and integrated into a distal end (10a, 100a) thereof, each of the image sensors being arranged to generate a sensor clock, which can be influenced by control electronics located at and integrated into a proximal end (10b, 100b) of the endoscope arrangement, wherein the distal end (10a, 100a) is spaced from the proximal end (10b, 100b), the control electronics is arranged for detecting the sensor clock at least one image sensor, of the plurality of image sensors, and for comparing a value of the sensor clock of the at least one image sensor, of the plurality of image sensors, with a corresponding value of another image sensor, of the plurality of image sensors, and adjusting the value of the one image sensor, of the plurality of image sensors, to the value of the other image sensor, of the plurality of sensors, and regulation of an image frequency and/or an image phase occurs by adjusting configuration data transmitted by the data line, each of the plurality of image sensors (11, 110) are electrically connected to the control electronics, located at the proximal end, via the data and power supply cable (17), and the sensor clock, for each one of the image sensors, is a local clock which is carried by the respective image sensor at the distal end of the endoscopic arrangement, and the control electronics, located at the proximal end of the endoscope arrangement, facilitates adjustment of each one of the sensor clocks, of the plurality of image sensors, by a signal received from a reference clock which is located external to the proximal end of the endoscopic arrangement.

14. An endoscopic arrangement (10, 100) with a plurality of image sensors (11, 110) located at and integrated into a distal end (10a, 100a) thereof, each of the image sensors being arranged to generate a sensor clock, which can be influenced by control electronics located at and integrated into a proximal end (10b, 100b) of the endoscope arrangement, wherein the distal end (10a, 100a) is spaced from the proximal end (10b, 100b), the control electronics is arranged for detecting a transmitted sensor frame rate or an image phase of at least one image sensor, of the plurality of image sensors, and for comparing a value of the transmitted sensor frame rate or transmitted image phase of the at least one image sensor, of the plurality of image sensors, with a corresponding value of another image sensor or image phase, of the plurality of image sensors, and adjusting the value of the at least one image sensor or image phase, of the plurality of image sensors, to the value of the other image sensor or image phase, of the plurality of sensors, and regulation of an image frequency and/or an image phase occurs by adjusting a sensor supply voltage transmitted by the power line and/or configuration data transmitted by the data line, each of the plurality of image sensors (11, 110) are electrically connected to the control electronics, located at the proximal end, via the data and power supply cable (17), and the sensor clock, for each one of the image sensors, is a local clock which is carried by the respective image sensor at the distal end of the endoscopic arrangement, and the control electronics, located at the proximal end of the endoscope arrangement, facilitates adjustment of each one of the sensor clocks, of the plurality of image sensors, by a signal received from a reference clock which is located at the control electronics located at and integrated into the proximal end (10b, 100b) of the endoscopic arrangement.

* * * * *